United States Patent [19]

Mills

[11] Patent Number: 5,132,118
[45] Date of Patent: Jul. 21, 1992

[54] TREATMENT OF EXERCISE-INDUCED PULMONARY HEMORRHAGE IN ANIMALS

[76] Inventor: John A. Mills, 2211 West 37th Avenue, Vancouver, B.C., Canada, V6M 1P2

[21] Appl. No.: 621,257

[22] Filed: Nov. 29, 1990

Related U.S. Application Data

[63] Continuation-in-part of Ser. No. 522,529, May 11, 1990, abandoned.

[51] Int. Cl.$^5$ ............................................. A61K 33/00
[52] U.S. Cl. ..................... 424/600; 424/601; 424/677; 424/679; 424/681; 424/683; 424/709; 424/713; 514/555; 514/708
[58] Field of Search ............... 424/677, 679, 681, 713, 424/600, 601, 709, 718, 600, 683; 514/588, 708

[56] References Cited

U.S. PATENT DOCUMENTS

| | | | |
|---|---|---|---|
| 4,296,104 | 10/1981 | Herschler | 424/679 |
| 4,405,596 | 9/1983 | Helbig et al. | 424/33 |
| 4,592,909 | 6/1986 | Winer et al. | 424/681 |

OTHER PUBLICATIONS

Callaghan et al, Equine Veterinary Journal, 1987, 19(5), 384–388.
Robinson, Equine Veterinary Journal, 1987, 19(5), 370–376.
Snow et al., The Veterinary Record, Apr. 17, 1982, 377–384.
Godwin et al., Quarterly Journal of Experimental Physiology (1984) 69, 49–59.

*Primary Examiner*—Allen J. Robinson
*Assistant Examiner*—Shailendra Kumar
*Attorney, Agent, or Firm*—Barrigar & Oyen

[57] ABSTRACT

A method and composition for the preventive and curative treatment of exercise-induced pulmonary hemorrhage in animals. The method comprises administration to the animal of a mixture of urea, alkaline potassium salts and magnesium salts. The composition comprises a mixture of urea, alkaline potassium salts, and magnesium salts, and if required, a pharmaceutically acceptable carrier.

22 Claims, No Drawings

TREATMENT OF EXERCISE-INDUCED PULMONARY HEMORRHAGE IN ANIMALS

This is a continuation-in-part of application Ser. No. 522,529, filed May 11, 1990, now abandoned.

FIELD OF THE INVENTION

This invention is directed to a method and composition useful for the preventative and curative treatment of exercise induced pulmonary hemorrhage in animals. More particularly, this invention relates to the health management of animal populations and to a method and composition for the prophylactic and curative treatment of exercise-induced pulmonary hemorrhage in animals, and, in particular, animals of the equine species, especially horses.

BACKGROUND OF THE INVENTION

Blood flowing from the nostrils of competitive Thoroughbred horses has been observed as far back as the sixteenth century. And despite over three hundred years of recognition, the condition has remained an enigma and until recently little has been attempted or achieved to uncover the underlying etiology and pathogenesis of this condition.

Historically, the source of blood at the nostrils was assumed to originate from within the nasal cavity because of the highly vascular nature of this organ. Post-exercise horses who exhibit blood at the nostrils are designated as "bleeders" and the condition termed "epistaxis", mistakenly analogous to epistaxis in man. However, two concepts emerged from observations of this condition, namely, that the blood originated in the nasal cavity, and that a positive relationship existed between bleeding episodes and poor competitive performance.

A recent retrospective survey of post-exercising horses with clinical evidence of blood at the nostrils positively identified the source of blood to have originated from the lungs. And repeated occurrences of pulmonary hemorrhage were precipitated by competitive exercise only. Further support of the hypothesis of the lung being the source of the blood was determined in horses with indwelling tracheostomy tubes that bled while being raced, the blood exiting the respiratory tract via the tracheostomy. By temporarily closing the tracheostomy, the blood flowed from the nostrils.

In the past, the paucity of diagnostic instrumentation which would allow safe examination of the equine upper respiratory tract with minimal restraint has been the primary factor impeding elucidation of this equine problem. The recent availability of the flexible fibreoptic endoscope into veterinary medicine has not only facilitated examination of the equine respiratory tract but has provided a means of locating the source of blood in bleeding horses.

The appearance of blood at the nostrils in exercising horses ranges from less than 1 to as high as 12 percent, but is generally about 0.5 to 2.5 percent. However, endoscopic surveys worldwide indicate that the actual prevalence of pulmonary hemorrhage is significantly higher than previously thought, with a range of 45 to 86 percent of racing or near maximal exercising horses. The incidence of pulmonary hemorrhage increases in direct proportion to the length of, and number of times, the endoscope is used on the individual animal. Histological examination of the caudal portion of the lung lobes revealed that 96 percent of horses that have raced had evidence of old alveolar hemorrhage.

The term used to describe the condition of pulmonary hemorrhage in horses without blood at the nostrils is exercise induced pulmonary hemorrhage (EIPH). EIPH is a more accurate description of bleeding in the racing horse than "bleeder". Multiple endoscopic surveys indicate that although pulmonary hemorrhage is experienced by a large number of racing or maximally exercising horses, epistaxis is a relatively infrequent manifestation of this phenomena. The frequency of occurrence of EIPH shows no relationship between the horse's sex, finishing position in the race, increasing age or distance raced. However, increased speed of exercise is directly associated with, and the common factor in, a higher incidence of EIPH in racing or maximally exercising horses.

Speeds greater than 240 meters per minute are necessary for a horse to have EIPH. The minimum speed required for a Standardbred to officially qualify to race competitively is about 755 meters per minute with the current world record about 885 meters per minute, whereas the average speed of racing Thoroughbreds is about 1050 meters per minute. EIPH occurs equally in both exercising Standardbreds and Thoroughbreds. However, the incidence of EIPH with epistaxis occurs only rarely in the racing Standardbred but more frequently in the racing Thoroughbred. Thus the speed of competition appears to be the constant factor designating whether a racing or maximally exercising horse will or will not have EIPH with epistaxis.

Repeated endoscopic examination of the same individual horse indicates that EIPH is not a random event but will repeatedly recur in the individual horse on a consistent basis. If a horse bleeds today, the chance of that same horse bleeding the next time it exercises or races is ten times higher than the horse who is not a bleeder. Periods of rest do not stop EIPH in horses. Upon return to training, and when maximal exercise form has been attained, bleeding recurs. Therefore, repeatability of EIPH is a consistent feature of this pathological phenomenon.

To determine the incidence of EIPH in post-racing horses, the animal was examined within 90 minutes of the completion of racing using a flexible fibreoptic endoscope. Both nostrils were examined for signs of hemorrhage. Other than the endoscopic observation of blood in the airways, a clear definitive set of clinical signs on which to establish a diagnosis of EIPH has not been documented. Astute horsemen report that horses with EIPH often have a distressed or anxious expression, "coolout" slowly, cough occasionally and swallow frequently. Coughing is not a consistent sign. Swallowing is a more consistent sign and is often the first indication of EIPH post-race. As the mucociliary blanket of the trachea clears the blood carried from the original source in the lungs, the blood pools on the floor of the larynx, flows onto the epiglottis, and then initiates the swallowing reflex.

Dyspnea is not commonly seen and if it occurs is a serious sign associated with extensive hemorrhage into the airways, exacerbation of pre-existing pulmonary disease or structural lung damage, ie. pulmonary abscess, pleural separation or tearing.

A characteristic pattern of clinical signs attributable to EIPH is further complicated by the variable response of the individual horse to the presence of blood in the airways. Moreover, the presence of blood at the nostrils is not a direct reflection of the severity of pulmonary hemorrhage or a determinant of the extent of the variability of performance noticeable upon initiation of pulmonary hemorrhage.

The major lesions of EIPH are multiple, separate and coalescing foci of moderately proliferative small airway disease accompanied by intense neo-vascularization of the bronchial circulation. These lesions are bilaterally symmetrical and confined to the dorsal angle of the lungs. Lesion extension occurs only along the dorsum of the lungs. Microscopic examination of the lungs of horses dying of EIPH has revealed engorgement of the pulmonary arteries, veins and capillaries, and rupture of the capillaries with hemorrhage into alveoli, bronchioles, bronchi, interstitium and subpleural tissue. The severity of engorgement and hemorrhage varied from almost nonexistent to massive in various areas of the lung, but the caudal portion of the lung lobes was the site of the most severe hemorrhage. Focally extensive pleural and interstitium fibrosis, and bronchiolitis were often accompanied by severe hemorrhage around large vessels and airways. Hemosiderophages also were present within this fibrous tissue, particularly at the junction of the pulmonary parenchyma and the deep layers of the pleura.

Latterly, numerous procedures have been performed in an attempt to prevent EIPH, with or without epistaxis, such as change of feed, bedding or ventilation, application of external or cold compresses to the nasal turbinate area, intermittent application of cold water over the thorax, and tying up the tail. More recently, various parenteral agents have been utilized in an effort to diminish the magnitude of EIPH in racing or near maximally exercising horses, namely atropine, estrogens, coagulants, clenbuterol (Ventipulmin TM), ipratropium (Atrovent TM), cromolyn (Intal TM), intravenous saline infusion and steam inhalation. Hesperidin-citrus bioflavinoids administered orally do not alter the prevalence of the pulmonary hemorrhage. Enforced rest, with a convalescence length much longer than three months duration, does not change the repeatability of the EIPH episodes which recur, with or without epistaxis, upon resumption of training and upon attaining maximal exercise form. But most of these techniques and treatments are no rarely utilized.

Currently, the sulfamoyl-anthranilic acid derivatives, for example, furosemide (Lasix TM) and ethacrynic acid, are parenterally administered to horses prior to racing in an attempt to control EIPH. Both of these drugs are potent diuretics which cause marked circulatory volume contraction in horses. The efficacy of these drugs in preventing EIPH has been extensively evaluated with widely variable results—sometimes stopping the hemorrhage, other times not stopping the hemorrhage, and yet at other times reducing the severity of the hemorrhage but not stopping the hemorrhage. Administration of these diuretics to horses having EIPH did not influence either the racing time or the systemic circulation physiology. However, administration of furosemide to horses negative for EIPH enhanced racing performance.

All the aforementioned procedures and drugs have been used in an attempt to prevent EIPH in exercising horses without fully understanding the underlying pathophysiology. EIPH, with or without epistaxis, in racing or maximally exercising Thoroughbred or Standardbred horses, causes greater financial losses than is encountered in other breeds of horses. Monetary loss following an EIPH episode ranges from slight to severe. EIPH occasionally can be fatal with affected horses dying almost instantaneously, this fatality often occurring during the latter portion of a race. But all affected EIPH horses are subject to an economic loss of some degree. In spite of a multiplicity of endeavours used to minimize EIPH in racing or maximally exercising horses, it remains today a major worldwide problem in the horse racing industry.

Commercially formulated horse diets for strenuously exercising animals contain only naturally occurring feed ingredients and thus have high protein and energy levels. The protein level is adequate without the addition of non-protein nitrogen (NPN) in any form. Usually, at time of manufacture, or immediately prior to feeding, the animal's diet may be supplemented with vitamins and minerals. Regardless of the time of supplementation, only small amounts of alkaline potassium salts, if at all, may be added to the manufactured feed. Potassium, in large concentration, is normally present in all forages, grains and grain by-products. The availability of potassium to simple stomached animals is about 85 to 90 percent. Thus an animal's recommended daily potassium requirement is readily acquired through the daily feed intake and potassium deficiency symptoms infrequently develop. Consequently, potassium supplementation of the horse's daily feed is neither routinely implemented nor required.

The following reference discloses subject matter which is relevant to exercise-induced pulmonary hemorrhage: M. W. O'Callaghan et al., "Exercise-Induced Pulmonary Hemorrhage in the Horse: Results of a Detailed Clinical, Post-Mortem and Imaging Study", Equine Veterinary Journal (1987) 19(5), 384-434.

SUMMARY OF THE INVENTION

This invention relates to the discovery that a mixture of urea, alkaline potassium salts and magnesium salts exhibits surprisingly effective activity against EIPH, and, in particular, is useful in the treatment of EIPH.

Specific compositions and methods of application of urea, alkaline potassium salts and optional magnesium salts mixtures have now been discovered. Use of such compositions and methods relate to the prophylactic and curative treatment of EIPH in animals, and in particular, in animals of the equine species, notably horses. These new methods comprise administration to animals of an effective amount of a mixture of urea, alkaline potassium salts and, if required, magnesium salts. More specifically, it is found that when urea-alkaline potassium salts and, optionally, magnesium salts compositions are administered orally to said animals, daily water intake increases, urine excretion increases by an increased glomerular filtration rate and the urine flow rate increases by an osmotic diuretic effect. Magnesium salts are required if the total daily feed consumed by the horse provides insufficient magnesium salts.

This invention specifically relates to a method for the suppression of EIPH in animals comprising administration to the animals of an effective amount of a mixture of urea, alkaline potassium salts and, if required, magnesium salts.

Representative compounds found useful in the prophylactic and curative treatment of EIPH in populations of animals, including affected members, comprise a mixture of urea and alkaline potassium salts and, if required, magnesium salts. Urea used in these formulations can be in the free base form or a pharmaceutically acceptable salt thereof. The following alkaline potassium salts are all well known and available commercially and have been found to be effective in treating horses in accordance with the present invention:

Potassium chloride
Potassium citrate
Potassium phosphate
Potassium nitrate
Potassium sulfate
Potassium acetate
Potassium gluconate
Potassium silicate Of the foregoing, potassium chloride appears to possess the most desirable therapeutic characteristics. Potassium chloride is advantageous because it is a non-toxic, non-corrosive, readily available, chemically stable compound.

The following magnesium salts are all well known and available commercially, and have been found to be effective in treating horses in accordance with the present invention:

Magnesium oxide
Magnesium hydroxide
Magnesium phosphate
Magnesium sulfate
Magnesium acetate
Magnesium chloride
Magnesium adipate
Magnesium lactate
Magnesium gluconate
Magnesium carbonate Of the foregoing, magnesium oxide appears to possess the most desirable therapeutic characteristics. Magnesium oxide is advantageous because it is a non-toxic, readily available, chemically stable compound.

In a particular aspect, the present invention relates to the prophylactic and curative treatment of EIPH in animals, including horses, and encompasses a method of prophylactic and curative therapy using a pharmaceutical composition, feed mixture, feed and liquid supplements containing a mixture of urea, alkaline potassium salts and, optionally, magnesium salts. In another aspect, this invention provides pharmaceutical and veterinary preparations and feed and liquid compositions for prophylactic and curative treatment of EIPH utilizing a mixture of urea, alkaline potassium salts and magnesium salts.

In broad terms, the invention is directed to a method for treating or preventing exercise-induced pulmonary hemorrhage in an animal which comprises administering to the animal a mixture of urea and pharmaceutically acceptable salts thereof, an alkaline potassium salt selected from the group consisting of potassium chloride, potassium citrate, potassium phosphate, potassium nitrate, potassium sulfate, potassium acetate, potassium gluconate and potassium silicate and, optionally, a magnesium salt selected from the group containing magnesium oxide, magnesium hydroxide, magnesium phosphate, magnesium sulfate, magnesium acetate, magnesium chloride, magnesium adipate, magnesium lactate, magnesium gluconate and magnesium carbonate.

In a particular embodiment, the urea can be in the free base form, the alkaline potassium salt can be potassium chloride and the magnesium salt can be magnesium oxide. The mixture can comprise about 1 to about 65 percent by weight urea, about 0.05 to about 50 percent by weight alkaline potassium salts and about 0.25 to about 25 percent by weight magnesium salts.

The alkaline potassium salt can be present in an amount ranging from about 0.05 to about 45 percent by weight, or more specifically from about 0.05 to about 35 percent by weight. Alternatively, the alkaline potassium salt can be present from about 0.25 to about 0.8 parts by weight per 1 part by weight of urea, or more specifically from about 0.6 parts by weight per 1 part by weight of urea The magnesium salt can be present in an amount ranging from about 1 percent to about 25 percent by weight. Alternatively, the magnesium salt can be present from about 0.05 to about 0.25 parts by weight of urea.

The mixture can be incorporated into a feed or liquid composition and fed to the animal on a daily basis. The mixture can be included in the daily diet of the animal in an amount between about 10 to about 1,000 g. The animal treated with the mixture can be a member of the equine species, and specifically a horse.

The invention is also directed to a composition for the prophylactic and curative treatment of exercise-induced pulmonary hemorrhage in an animal comprising: (a) urea or a pharmaceutically acceptable salt thereof; (b) an alkaline potassium salt selected from the group consisting of potassium chloride, potassium citrate, potassium phosphate, potassium nitrate, potassium sulfate, potassium acetate, potassium gluconate, potassium silicate; and (c) a magnesium salt designated from the group consisting of magnesium oxide, magnesium hydroxide, magnesium phosphate, magnesium sulfate, magnesium acetate, magnesium adipate, magnesium lactate and magnesium gluconate.

The urea can make up about 1 to about 65 percent by weight of the composition, the alkaline potassium salt can make up about 0.05 to about 45 percent by weight of the composition and the magnesium salt can make up about 1 to about 25 percent by weight of the composition. The alkaline potassium salt can be potassium chloride and can be present in the composition in an amount ranging from about 0.05 to about 35 percent by weight of the composition. The ratio of urea to potassium chloride can be about 1 part by weight urea to about 0.6 parts by weight potassium chloride. Urea and the potassium chloride can be mixed with a pharmaceutically acceptable carrier. The magnesium salt can be magnesium oxide and can be present in the composition in an amount ranging from about 1 to 10 percent by weight of the composition. The ratio of urea to magnesium oxide can be about 1 part by weight urea to about 0.16 parts by weight magnesium oxide. Urea and magnesium oxide can be mixed with a pharmaceutically acceptable carrier. Urea, potassium chloride and magnesium oxide can be mixed with a pharmaceutically acceptable carrier.

DETAILED DESCRIPTION OF SPECIFIC EMBODIMENTS OF THE INVENTION

The urea used in the practice of this invention can be in the free base form or in the form of a pharmaceutically acceptable salt. For example, urea may be readily converted to one of its nontoxic acid addition salts by customary methods used in the chemical art. Nontoxic salts of this invention can be formed from free base urea and an acid which is pharmaceutically acceptable in the intended dosages. Such salts include those prepared from inorganic acids, organic acids, higher fatty acids, higher molecular weight acids, and the like. Exemplary acids are hydrochloric acid, hydrobromic acid, sulfuric acid, nitric acid, phosphoric acid, methane sulfonic acid, benzene sulfonic acid, acetic acid, propionic acid, malic acid, succinic acid, glycolic acid, lactic acid, salicylic acid, benzoic acid, nicotinic acid, phthalic acid, stearic acid, oleic acid, abietic acid, and the like.

The amount of urea in such preparations may be as little as 1 percent by weight or as high as about 50 percent by weight. Below 1 percent by weight, the urea is generally too low to be therapeutically useful. The upper limit of about 50 percent by weight is based on the solubility limit of urea in water.

The amount of alkaline potassium salts added to the preparation should be in the range of about 0.05 to 50 percent by weight. Below about 0.05 percent by weight, the alkaline potassium salts are generally ineffective. Amounts of alkaline potassium salts in excess of about 50 percent by weight have been found to be unnecessary and wasteful. Generally no more than about 45 percent by weight, and preferably, no more than about 42 percent by weight of alkaline potassium salts are used. As a general rule, the amount of alkaline potassium salts used is based on the amount of urea used. Good results are obtained when the amount of alkaline potassium salt is about 25 to 80 percent by weight of the weight of urea in the preparation, with alkaline potassium salts at about 35 percent by weight of urea providing particularly good results.

The following alkaline potassium salts are generally effective in the prophylactic and curative treatment of EIPH in horses
Potassium chloride
Potassium citrate
Potassium phosphate
Potassium nitrate
Potassium sulfate
Potassium acetate
Potassium gluconate Of these, potassium chloride, hereinafter referred to simply as KCl, is usually the most suitable for use in pharmaceutical compositions, feed mixtures, feed and liquid supplements for the prophylactic and curative treatment of EIPH in the equine species, including horses.

The amount of magnesium salts added to the preparation should be in the range of about 1 to about 25 percent by weight. Below about 1 percent by weight, the magnesium salts are ineffective. Amounts of magnesium salts above 25 percent are wasteful and unnecessary. Generally, no more than about 20 percent by weight, and preferably, no more than about 15 percent by weight of magnesium salts are used. Good results are obtained when the amount of magnesium salt is about 5 to about 25 percent by weight of the urea in the preparation, with magnesium salts at about 10 percent by weight of urea providing particularly good results.

The following magnesium salts are generally effective in the prophylactic and durative treatment of EIPH in horses:
Magnesium oxide
Magnesium hydroxide
Magnesium phosphate
Magnesium sulfate
Magnesium acetate
Magnesium chloride
Magnesium adipate
Magnesium lactate
Magnesium gluconate
Magnesium carbonate Of these, magnesium oxide, hereinafter referred to simply as MgO, is usually the most suitable for use in pharmaceutical compositions, feed mixtures, feed and liquid supplements for the prophylactic and curative treatment of EIPH in the equine species, including horses.

The compounds defined above are readily absorbed into the blood stream from the stomach and intestinal tract of the treated animal when taken orally, and therefore the preferred method of treatment is to administer the compound orally to the animal. This is also the safest, simplest and most practical route of administration. Optional modes can be used where, for example, the animal is not eating or cannot swallow or has difficulty in swallowing. Other acceptable methods of administration which permit the compound to be absorbed in the gastrointestinal tract or which deliver a solution of the compound directly to the bloodstream (intravenous injection) can then be employed.

The method of administration may also vary depending on the purpose of administration. For example, use as a prophylaxis or preventative treatment or as a treatment of affected animals can require different methods of treatment and dosage forms easily formulated by those skilled in the art.

The dosage regimen in carrying out this invention utilizing the urea—KCl—MgO mixture for treatment of EIPH of horses are those which insure maximum therapeutic response. The average effective daily dose of the urea—KCl—MgO mixture is between about 100 mg/kg to about 2000 mg/kg of body weight, with about 600 to about 1250 mg/kg of body weight being preferred.

The treatment of animals can normally be accomplished by incorporating an effective amount of the compound in the animal's diet as a solid or liquid feed supplement, or dissolved in the animal's liquid intake. The urea—KCl—MgO mixture for use in the practice of the present invention includes compounds which are non-toxic to the animals, including horses, when administered daily to the animal in the animal's feed diet in concentrations of about 10 to about 1,000 g. Anti-EIPH effects can be realized also for the various urea, alkaline potassium salts and magnesium salts when administered daily in the animal's feed diet in concentrations of about 10 to about 1,000 g.

Compositions useful in the practice of the present invention can be prepared in forms suitable for administration by compounding an effective single dose amount of the compound with known pharmaceutically acceptable carrier ingredients generally employed in the preparation of theurapeutic compositions of the type which are provided as tablets, hard capsules, powders, granules and aqueous suspensions.

Compositions intended for oral use may be prepared according to methods known generally in the art. Such compositions may contain one or more pharmaceutically acceptable carrier agents selected from the group consisting of sweetening agents, flavoring agents, coloring agents and preserving agents. In general, the composition will contain a mixture of urea, alkaline potassium salts and magnesium salts in admixture with non-toxic pharmaceutically acceptable excipients. Exemplary excipients are: interdilutants such as calcium carbonate, sodium carbonate, lactose, calcium phosphate, and sodium phosphate; granulating or disintegrating agents, for example, maize, starch, and algenic acid; binding agents, for example, starch, gelatin and acacia; and lubricating agents, for example magnesium stearate, stearic acid, and talc. Tablets may be uncoated or they may be coated by known techniques to make them more therapeutically effective, for example, to delay disintegration or absorption, or to make them more palatable, or for other reasons for which orally administered mixtures of urea, alkaline potassium salts and magnesium salts have been previously provided in coated form.

Formulations for oral use may also be presented as hard gelatin capsules wherein the mixture of urea, alkaline potassium salts and magnesium salts is admixed with an inert solid diluent, for example, calcium carbonate, calcium phosphate and kaolin.

Aqueous solutions containing a mixture of urea, alkaline potassium salts and magnesium salts can also be utilized, when desirable. Excipients suitable for aqueous suspensions may be employed, if desired. Such excipients include: suspending agents, for example, sodium carboxmethylcellulose, methylcellulose, hydroxypropylmethylcellulose, sodium alginate, polyvinylpyrrolidone, gum tragacanth and gum acacia; dispersing or wetting agents which may be a naturally occurring phosphatide, for example, lecithin, condensation products of an alkylene oxide with fatty acids, for example, polyoxyethylene stearate, condensation products of ethylene oxide with long-chain aliphatic alcohols, for example, heptadecaethyleneoxy-cetanol, condensation products of ethylene oxide with partial esters derived from fatty acids and a hexitol, for example polyoxyethylene sorbitol monoleate, and condensation products of ethylene oxide with partial esters derived from fatty acids and hexitol anhydrides, for example, polyoxyethylene sorbitan monoleate. The said aqueous suspensions may also contain one or more preservatives, for example, ethyl, or n-propyl-p-hydroxy benzoate, one or more coloring agents, one or more flavouring agents, and one or more sweetening agents such as sucrose.

Dispersible powders and granules suitable for preparation of an aqueous suspension by the addition of water provide the mixture of urea, alkaline potassium salts and magnesium salts in admixture with dispersing, suspending or wetting agent. Additional excipients, for example, sweetening, flavoring and coloring agents may also be present.

The pharmaceutical compositions may be in the form of a sterile injectionable preparation, for example, as a sterile injectable aqueous suspension. This suspension may be formulated according to available art methods using suitable dispersing or wetting agents and suspending agents such as those which have been mentioned above, or others. This sterile injectable preparation may also be a sterile injectable solution or suspension in a non-toxic parenterally acceptable diluent or solvent, for example, as an aqueous solution buffered to a pH of about 4.0 to 7.0 and made isotonic with sodium chloride.

Further, the mixture of urea, a single alkaline potassium salt and a single magnesium salt may be administered alone or in admixture with a mixture of urea other alkaline potassium salts and other magnesium salts, or with other agents having the same, similar or different pharmacological properties.

The following examples of preferred embodiments of this invention, showing veterinary and pharmaceutical compositions, were all prepared using urea, KCl and MgO. Similar granules, capsules, tablets, feed and liquid supplements can be prepared containing other of the designated alkaline potassium salts and magnesium salts.

DESCRIPTION OF PREFERRED EMBODIMENTS

Compositions containing urea—KCl—MgO mixtures in dry powder or granular form should generally contain only about 65 weight percent of urea and preferably no more than about 58 weight percent; and should generally contain only about 50 weight percent of KCl and preferably no more than about 35 weight percent, and should generally contain only about 25 weight percent of MgO and preferably no more than about 10 weight percent.

Formulations containing urea—KCl—MgO preparations in aqueous solution should generally contain only about 50 weight percent of urea and preferably no more than about 35 weight percent, and should generally contain only about 25 weight percent of KCl and preferably no more than about 20 weight percent and should generally contain only about 20 weight percent of MgO and preferably no more than about 10 weight percent.

The following examples are provided to illustrate the activity of various urea—KCl—MgO formulations in the prophylactic and curative treatment of EIPH in racing or maximally exercising horses. The examples are not to be taken as an exhaustive list of the possible methods and compositions for using the urea—KCl—MgO formulations and the benefits resulting from their use. The examples do, however, give some indication of the broad scope of this invention, specifically, the suitability of urea—KCl—MgO preparations for a variety of situations.

EXAMPLE 1

A series of blood samples were collected from various horses to demonstrate that in the Thoroughbred and Standardbred breeds of racing horses elucidation of the etiopathogenesis and verification of EIPH through implementation of hematology and biochemical screening procedures are uninformative and valueless. Even though both breeds are exposed to a wide variety of environmental conditions throughout the world the incidence of bleeding from the nostrils, ie. epistaxis, is greater in the Thoroughbred than the Standardbred breed.

It is thought that the occurrence of bleeding in racing or maximally exercising horses may be caused by an inherited genetic factor which is expressed more often in Thoroughbreds than Standardbreds. However, the incidence of EIPH in both breeds of horses varies similarly statistically (between 45 to 86 percent) and anatomically (caudal diaphragmatic lung lobes), whereas the incidence of bleeding in Thoroughbreds varies from less than 1 up to 12 percent but occurs only rarely in Standardbreds.

Thus the disparity in the incidence of bleeding between these two breeds of racing horses may be due to either: (1) genetic differences between the hematology and biochemical values, or (2) the speed of racing or maximally exercising.

To examine the possibility of a heritable genetic difference occurring between the hematological and biochemical levels of racing Thoroughbred and Standardbred horses a series of blood samples were collected from eight racing Thoroughbreds and eight racing Standardbreds for laboratory analysis and the results recorded.

The age of the eight racing Thoroughbreds in this test ranged between 3 to 7 years with an average age of 4.2 years, body weight ranged between 420 and 468 kg. with an average of 444 kg. The eight racing Standardbred horses ranged in age between 2 to 9 years with an average of 3.5 years, body weight ranged between 397 and 470 kg. with an average of 439 kg.

The average hematogolical and biochemical levels of the said test horses are listed below:

| Hematology and Biochemistry | Standardbred n = 8 | Thoroughbred n = 8 | Units |
|---|---|---|---|
| White cell count | 7.3 | 6.9 | th/mm$^3$ |
| Red cell count | 7.7 | 8.4 | mil/mm$^3$ |
| Hemoglobin | 12.9 | 13.0 | g/dl |
| Hematocrit | 33.9 | 30.6 | % |
| Platelet count | 180 | 174 | th/mm$^3$ |
| Glucose | 63 | 64 | mg/dl |
| Blood urea nitrogen | 22 | 14 | mg/dl |
| Creatinine | 1.6 | 1.5 | mg/dl |
| Sodium | 141 | 138 | meq/dl |
| Potassium | 3.5 | 3.7 | meq/dl |
| Calcium | 12.2 | 11.8 | mg/dl |
| Phosphorus | 3.4 | 3.6 | mg/dl |
| Total protein | 6.0 | 5.5 L* | g/dl |
| Albumin | 3.5 | 3.6 | g/dl |
| Globulin | 2.5 | 1.9 L | g/dl |
| Bilirubin total | 2.0 | 2.2 | mg/dl |
| Albumin/Globulin ratio | 1.4 | 1.9 H | |
| Calculated Osmolality | 281 | 272 | |
| Chloride | 100 | 100 | meq/l |
| Carbon dioxide | 29 | 26 | meq/l |
| Anion gap | 12 | 12 | |
| Cholesterol | 91 | 102 | mg/dl |

*L - Lower than normal value
H - Higher than normal value

Comparison of the measured hematological and biochemical parameters between the two breeds of racing horses indicates that there is a striking similarity between the two sets of hematological and biochemical values for Thoroughbred and Standardbred horses rather than a distinct demonstrable difference. Since the incidence of EIPH in Thoroughbreds and Standardbreds is similar, it appears from these examples that the difference in the incidence of EIPH with epistaxis between racing Thoroughbreds and Standardbreds must be directly related to the speed of racing and is not a visible expression of a heritable genetic factor. The probability of speed being a factor in having EIPH, with or without epistaxis, has credence since it has been found that a speed greater than 240 meters per minute is necessary to produce EIPH and that the average speed of racing Thoroughbreds is about 1050 meters per minute, whereas the world record speed of a Standardbred pacer is about 885 meters per minute.

EXAMPLE 2

This example illustrates the effect of daily oral feeding in the grain ration of a dry urea—KCl—MgO composition to eliminate or prevent EIPH in a 5 year old Standardbred mare, 440 kg. body weight, with a long history of EIPH episodes occurring during racing. The mare is currently racing with a pre-race intravenous bleeder injection to prevent EIPH during the race.

A dry feed supplement intended as a feed for racing and maximally exercising horses was prepared by blending about 4 percent weight of urea, about 3 percent weight of KCl and about 0.2 percent weight of MgO in a basic performance-type horse ration containing:

| Ingredient | Amount |
|---|---|
| Oats, whole | 4767 g |
| Soybean Oil Meal | 113 g |
| Sweet Feed, 12% C.P. | 1589 g |
| Salt, Cobalt-Iodized | 60 g |
| Dicalcium Phosphate | 60 g |
| Vitamins and Minerals | 75.0 g |
| Vitamin A | 67500 I.U. |
| Vitamin D | 18000 I.U. |
| Vitamin E | 180 I.U. |
| Vitamin B12 | 180 mcg |
| Niacin | 187.5 mg |
| Thiamine | 37.5 mg |
| Riboflavin | 60.0 mg |
| Pantothenic Acid | 75.0 mg |
| Choline Chloride | 1.125 g |
| Folic acid | 18.0 mg |
| Iodine | 1.5 mg |
| Manganese Sulphate | 506.25 mg |
| Zinc Oxide | 1.5 g |
| Cobalt Sulphate | 11.25 mg |
| Copper Sulphate | 112.5 mg |
| Ferrous Sulphate | 1.125 g |
| Fluorine (max) | 150.0 mg |

The total daily feed intake consisted of about 13 pounds (5.9 kg) of timothy hay, about 3.3 pounds (1.5 kg) of alfalfa cubes, about 11.25 pounds (5.1 kg) of whole oats and about 3.75 pounds (1.8 kg) of commercially mixed grain to which was added the dry urea—KCl—MgO composition at a level of about 4 percent weight of urea, about 3 percent weight of KCl and about 0.2 weight percent of MgO. Salt (NaCl) was added at a level of supplementation to provide the test animal a total daily intake of about 1600 mEq Na$^+$. Supplementation of the daily grain ration with about 4 weight percent of urea, about 3 weight percent of KCl and about 0.2 weight percent of MgO provided the test animal a total daily intake of about 4200 mEq of urea, about 6200 mEq of K$^+$ and about 3000 mEq of Mg$z^{2+}$.

The dosage regimen in carrying out this test, where the said composition was used for the prophylactic or curative therapy of EIPH during racing or maximal exercise in horses, was used to insure maximum therapeutic response.

The effective daily dosage attained by the animal for the active ingredient urea of this invention was between about 475 mg/kg body weight to about 550 mg/kg body weight, and for KCl was between about 335 mg/kg to about 375 mg/kg body weight, and for MgO was between about 70 mg/kg body weight to about 80 mg/kg body weight.

Demonstrable effectiveness for this route of administration of this invention in preventing or eliminating EIPH during racing or maximal exercise in a horse is illustrated by the race results produced by this 5 year old Standardbred mare in a total of thirteen consecutive officially sanctioned harness races.

The thirteen races which were run during the spring and summer racing season by the 5 year old Standardbred mare were all performed within a single class of competition. The first three races of this series were run with the usual preface intravenous bleeder injection. The next seven races were performed without a pre-race intravenous bleeder injection but with the said composition supplemented at maximum therapeutic level in the daily grain ration. The final three races of this series again were run with only a pre-race intravenous bleeder injection and without the supplementation of the said composition. The economic placement, total monetary winnings and winnings per start for the thirteen races are listed below:

|  | Economic Placement | | | | | | | Total Monetary Earnings ($) | Monetary Returns Per Start ($) |
| --- | --- | --- | --- | --- | --- | --- | --- | --- | --- |
| Races | 1 | 2 | 3 | 4 | 5 | No. | (%) | | |
| Six races - pre-race intravenous bleeder injection | 1 | — | 1 | — | 1 | 3/6 | 50 | 1,656 | 276 |
| Seven races - daily urea-KCl—MgO composition | 1 | 3 | 1 | — | 1 | 5/7 | 71 | 3,140 | 448 |

Winnings per start in this series of thirteen races increased by more than 62 percent with the addition of the said composition to the daily grain ration over the use of a pre-race intravenous bleeder injection for prevention of EIPH during the race.

No evidence of EIPH was observed in this horse while racing, or after racing, or during the entire seven races while consuming the dry urea—KCl—MgO formulation at maximum therapeutic level in the daily grain ration.

Urine samples, collected from the first and second place winners by authority of the Federal Racing Commission, were laboratory tested for the presence of illegal performance enhancing drugs and were always certified negative and the tests were never masked or compromised by the oral use of this invention.

During the time the said preparation was supplemented in the daily grain ration there was a noticeable improvement in the horse's demeanor, power, endurance and speed during training which carried over to surprisingly influence the official race results. Upon cessation of daily intake of this invention, the horse rapidly reverted to the previous level of performance.

Use of dry urea—KCl—MgO composition added to the daily grain ration at a sufficient level to ensure maximum therapeutic response eliminated or prevented EIPH in a horse with a long standing history of EIPH occurring during racing.

EXAMPLE 3

The effectiveness of dry urea—KCl—MgO composition in treating and preventing EIPH in a 4 year old Standardbred mare, 428 kg body weight, with a long history of EIPH occurring during racing was determined. The mare was currently utilizing a pre-race intravenous bleeder injection for the prevention of EIPH during racing.

The dry urea—KCl—MgO composition, as well as supplemental NaCl, were admixed into the daily grain ration so that about 4 weight percent of urea, about 3 weight percent of KCl and about 0.2 weight percent of MgO were consumed by the test animal. In addition, about 3.3 pounds (1.4 kg) of alfalfa cubes and about 12 pounds (5.5 kg) of alfalfa-timothy mixed hay were the daily roughage intake of the daily ration.

The effective dosage of the composition consumed daily by the test animal was between about 500 mg/kg body weight to about 585 mg/kg body weight for urea, was between about 200 mg/kg body weight to about 375 mg/kg body weight for KCl and was between about 50 mg/kg to about 60 mg/kg for MgO. The dosage was preferably no more than about 575 mg/kg body weight of urea, about 350 mg/kg body weight of KCl and about 55 mg/kg body weight of MgO. The daily ration supplemented with this invention provided a daily intake of about 4200 mEq of urea, about 6000 mEq of $K^+$ and about 2400 mEq of $Mg^{2+}$. The supplemental NaCl provided the test animal a total daily intake of about 1500 mEq $Na^+$. The dosage regimen of the said composition was such as to ensure maximum therapeutic response in treating and preventing the occurrence of EIPH in a 4 year old Standardbred mare with a long standing history of EIPH occurring while racing.

The effectiveness of this invention in preventing and treating an EIPH prone animal and the competitive racing results resulting therefrom are documented below.

Initially, four races at the start of the autumn racing meet were completed with a pre-race intravenous bleeder injection which resulted in no EIPH episodes and a single economic placement (5th). Subsequently, a two month rehabilitation period away from the racetrack environment intervened. Upon return to racing, a series of nine consecutive races were run in a single competitive class. The first six races were performed using a pre-race intravenous bleeder injection as a protective measure against EIPH whereas the final three races were performed without a pre-race intravenous bleeder injection but with the maximum therapeutic dosage of dry urea-KClMgO composition being consumed daily in the grain ration to prevent or eliminate EIPH during racing.

The dry urea—KCl—MgO composition was slowly introduced into the daily grain ration and maximum therapeutic dosage was reached only after the eighth day. Full dosage was reached twelve days before the sixth race and was maintained at that dosage level until completion of the test.

No gastrointestinal upset or colic occurred during the test and daily grain consumption and palatability were unaffected with admixture of this invention. A noticeable increase in water intake and increased urine excretion were obvious before the third day of supplementing the daily grain ration with this invention. Both of the aforementioned physiological parameters increased in quantity until full daily dosage was reached and remained at that elevated level until cessation of the test. Before the second day after the end of the test both the quantities of water consumed and urine produced noticeably decreased and returned to more normal amounts for a racing horse not fed the composition of this invention.

Two blood samples were collected for determination of hematological and biochemical parameters. The first blood sample was obtained after the sixth race and before the start of feeding the said composition in the daily grain ration, and the second blood sample was collected after the ninth race and the completion of the test. The laboratory values obtained for hematology and biochemistry of the two blood samples are listed below.

| Hematology and Biochemistry | Blood Sample 1 Day 0 | Blood Sample 2 Day 29 | Units |
| --- | --- | --- | --- |
| White cell count | 7.0 | 7.1 | th/mm³ |
| Red cell count | 8.7 | 10.0 | mil/mm³ |
| Hemoglobin | 14.1 | 16.1 | g/dl |
| Hematocrit | 36.4 | 42.1 | % |
| Platelet count | 170 | 180 | th/mm³ |
| Glucose | 55 L* | 62 | mg/dl |
| Blood urea nitrogen | 15 | 17 | mg/dl |
| Creatinine | 1.6 | 1.5 | mg/dl |
| Sodium | 146 | 139 | meq/dl |
| Potassium | 3.7 | 3.8 | meq/dl |
| Calcium | 12.9 | 12.9 | mg/dl |
| Phosphorus | 2.4 L | 3.1 | mg/dl |
| Total protein | 5.6 L | 6.2 | g/dl |
| Albumin | 3.5 | 3.3 | g/dl |
| Globulin | 2.1 L | 2.9 | g/dl |
| Bilirubin total | 1.8 | 1.3 | mg/dl |
| Albumin/Globulin ratio | 1.7 H | 1.1 | |
| Calculated Osmolality | 287 | 275 | |
| Chloride | 103 | 100 | meq/l |
| Carbon dioxide | 36 H | 26 | meq/l |
| Anion gap | 7 | 13 | |
| Cholesterol | 85 | 95 | mg/dl |

*L - Lower than normal value
H - Higher than normal value

The economic placement, monetary winnings and monetary returns per start for the entire nine races, the six races run with a pre-race intravenous bleeder injection and the three races competed with only this invention supplemented into the daily grain ration are listed below:

| Races | Economic Placement 1 | 2 | 3 | 4 | 5 | No. | (%) | Total Monetary Earnings ($) | Monetary Returns Per Start ($) |
| --- | --- | --- | --- | --- | --- | --- | --- | --- | --- |
| Nine - total | 1 | 1 | 1 | 1 | 2 | 6/9 | 66 | 1,931 | 214 |
| Six - pre-race intravenous bleeder injection | 1 | — | — | — | 2 | 3/6 | 50 | 1,195 | 199 |
| Three - daily urea-KCl—MgO composition | — | 1 | 1 | 1 | — | 3/3 | 100 | 736 | 245 |

It specifically appears from the race results that with no change in management procedures other than the supplementation of the daily grain ration with this invention, the monetary return per start increased more than 23 percent over that attained with a pre-race intravenous bleeder injection. It is logical to conclude that the increased economic returns and absence of EIPH occurring during racing are directly related to the daily intake of this invention in the animal's daily grain ration.

Observable clinical manifestations of colic, gastrointestinal and endocrinological abnormalities were not apparent from close observation of the test animal during the test period.

Throughout the twenty-nine day test period, with supplementation of the daily grain ration with the dry urea—KCl—MgO composition, and during or after many training sessions and during or after competing in three officially sanctioned races, no characteristic clinical signs of, or endoscopic evidence of EIPH, developed in this 4 year old Standardbred mare, which previously had a long history of EIPH occurring while racing.

As this example illustrates, not only is EIPH eliminated or reduced in a 4 year old racing Standardbred mare with a long history of EIPH episodes occurring while racing, but specifically also demonstrates the suitability of this invention to enhance an animal's racing or maximal exercising performance up to its genetic potential.

EXAMPLE 4

The safety of long-term administration and possible cumulative effects of the urea—KCl—MgO composition in aqueous solution when given daily and orally for a 282 day period at maximum therapeutic dosage for the prevention or elimination of EIPH in a 4 year old Standardbred gelding, 450 kg body weight, during the pre-race training period and official harness race meet was investigated. Hematological and biochemical values obtained from four blood samples were compared to determine if the measured parameters were pathophysiologically altered by the long-term daily consumption of the said composition admixed into the daily grain ration.

The animal's daily feed intake consisted of about 3.3 pounds (1.4 kg) of alfalfa cubes and about 10 pounds (4.5 kg) of alfalfa hay for roughage and grain, about 11 pounds (5 kg) of whole oats and about 3.5 pounds (1.5 kg) of commercial mixed grain (see Example 2).

The daily dosage of the said composition in aqueous solution provided the test animal with between about 485 mg/kg body weight and about 550 mg/kg body weight of urea and for KCl between about 260 mg/kg body weight and about 350 mg/kg body weight. Thus, the test animal was provided with a total daily intake of about 4200 mEq of urea and about 6400 mEq of K+. NaCl was supplemented daily to the test animal to provide a total daily intake of about 1500 mEq Na+. MgO was supplemented daily to the test animal to provide a total daily intake of about 3300 mEq of $Mg^{2+}$.

At various times during the 282 day test period, the aqueous solution was supplied to the test animal in the drinking water, admixed into the oats and mixed grain or poured onto the alfalfa hay or cubes. Palatability of this composition was unaffected regardless of the route of administration. The test animal did not react adversely to the various oral routes of intake nor at any time throughout this test period show any physical discomfort or clinical evidence of gastrointestinal upset or colic.

The hematological and biochemical levels obtained from blood samples collected: (1) immediately prior to the start of the long-term feeding test of the said composition in aqueous solution (Day 0); (2) midway during the training period (Day 168); (3) immediately prior to the start of the race meet (Day 203); (4) several days after the eighth race of the race meet (Day 245); and, (5) two days after the eleventh race of the race meet (Day 282), are listed below:

|  | Blood Sample | | | | | |
|---|---|---|---|---|---|---|
|  | 1<br>Day 0 | 2<br>Day 168 | 3<br>Day 203 | 4<br>Day 245 | 5<br>Day 282 | Units |
| Hematology and Biochemistry | | | | | | |
| White cell count | 8.8 | 8.3 | 6.1 | 6.8 | 7.6 | th/mm$^3$ |
| Red cell count | 7.10 | 9.10 | 8.3 | 8.0 | 8.7 | mil/mm$^3$ |
| Hemoglobin | 12.0 | 15.1 | 13.9 | 13.4 | 14.7 | g/dl |
| Hematocrit | 31.1 L* | 40.9 | 37.1 | 36.2 | 39.7 | % |
| Platelet count | 210 H | 160 | 160 | 170 | 170 | th/mm$^3$ |
| Glucose | 54 L | 80 | 89 | 94 | 84 | mg/dl |
| Blood urea nitrogen | 24 | 23 | 22 | 24 | 23 | mg/dl |
| Creatinine | 1.6 | 1.5 | 1.6 | 1.5 | 1.6 | mg/dl |
| Sodium | 143 | 140 | 137 | 143 | 142 | meq/dl |
| Potassium | 2.8 | 3.6 | 3.7 | 4.0 | 3.8 | meq/dl |
| Calcium | 12.6 | 12.4 | 12.1 | 12.0 | 11.6 | mg/dl |
| Phosphorus | 4.4 | 4.2 | 3.4 | 4.0 | 3.8 | mg/dl |
| Total protein | 6.0 | 6.0 | 6.1 | 6.0 | 6.6 | g/dl |
| Albumin | 3.5 | 3.3 | 3.5 | 3.6 | 3.8 | g/dl |
| Globulin | 2.5 | 2.7 | 2.6 | 2.4 | 2.8 | g/dl |
| Bilirubin total | 2.6 | 2.5 | 2.9 | 2.6 | 3.1 | mg/dl |
| Albumin/Globulin ratio | 1.4 | 1.2 | 1.3 | 1.5 | 1.4 | |
| Calculated osmolality | 283 | 280 | 275 | 287 | 284 | |
| Chloride | 99 | 101 | 101 | 107 | 103 | meq/l |
| Carbon dioxide | 26 | 24 | 24 | 23 | 26 | meq/l |
| Anion gap | 18 H | 15 | 12 | 13 | 13 | |
| Cholesterol | 102 | 128 | 127 | 137 H | 124 | mg/dl |
| Protein Electrophoresis | | | | | | |
| Albumin | 3.30 | 3.30 | 3.60 | 3.40 | 3.80 | g/dl |
| Alpha-1 Globulin | 0.03 L | 0.10 H | 0.30 H | 0.20 H | 0.10 H | g/dl |
| Alpha-2 Globulin | 0.50 | 0.40 | 0.10 L | 0.10 L | 0.40 | g/dl |
| Beta-1 Globulin | 0.30 L | 0.50 | 0.40 | 0.40 | 0.60 | g/dl |
| Beta-2 Globulin | 0.50 | 0.30 | 0.50 | 0.50 | 0.30 | g/dl |
| Gamma Globulin | 1.20 | 1.40 | 1.20 | 1.20 | 1.20 | g/dl |

*L - Lower than normal value
H - Higher than normal value

These results demonstrate the safety of long-term administration of this invention at a dosage regimen to produce maximum therapeutic effect. It is also evident that the hematological and biochemical levels obtained prior to the administration of this invention progressively increase with continuous feeding into a normal equine hematological and biochemical profile, even though some of the initial values are outside the normal physiological range. From this sampling, it is logical to conclude that cumulative toxic effects attributable to the long-term daily intake of the above defined composition, and consumed at the indicated dosage regimen, are non-existent and physiologically unapparent.

The protein electrophoretic values in the plasma from the serial blood samples illustrate that the albumin level markedly increases with the start of competitive racing. With the start of daily feeding of this invention, both the alpha-1 and beta-1 globulin fractions are increased to normal physiological values. Long-term feeding of this invention substantially increases the alpha-1 globulin fraction while the alpha-2 globulin fraction at first declines to a lower than normal physiological value and then rises to a normal physiological level. The beta-1, beta-2 and gamma fractions remain within their respective normal physiological range throughout the 282 day test even though the animal was continuously raced during this test.

The obvious visible signs of EIPH have not occurred in the test animal during either the many training sessions or the official races run in the current race meet while ingesting this invention admixed into the daily feed ration.

An unexpected discovery has been made from these results. It specifically appears that even with the relatively high levels of dietary crude protein (12 to 14 percent) present in the ration of racing horses, the level of nitrogen retention is significantly enhanced by gu microflora utilizing the NPN contained in this invention. Urea is largely excreted by the kidney into the urine before any recycling can occur. However, some urea recycling occurs into the large intestine and cecum where it is hydrolyzed into ammonia ($NH_3$) and carbon dioxide ($CO_2$) by urease enzyme, a product of plant and bacterial origin. The $NH_3$ is then utilized by the intestinal and cecal microflora for the synthesis of protein. Cecal microbial protein is hydrolyzed to yield amino acids (both essential and non-essential amino acids which may be lacking in the diet) which are then absorbed into the blood plasma where they can be utilized by the liver for synthesis of protein. This specifically appears to be what is occurring when the abnormal hematological and biochemical values of this test animal are normalized and improved with the daily intake of this invention even while continuously racing.

The invention is therefore not only useful in the prevention or elimination of EIPH. But when this invention is fed daily to racing or maximally exercising horses, there is a simultaneous normalization of hematological and biochemistry values and a substantially marked improvement in the speed, stamina and performance of the animal.

Another unexpected discovery following from the results obtained above was that since proteins are the only dissolved substances in the plasma that do not readily diffuse into the interstitial fluid, and only those substances that fail to pass through the pores of a semi-permeable membrane exert osmotic pressure, it is the dissolved proteins of the plasma and interstitial fluids that are responsible for the osmotic pressure at the capillary membrane. Thus colloid osmotic pressure of the plasma is caused by the dissolved proteins and since the concentration of dissolved plasma proteins substantially increases with the daily consumption of this invention, there develops simultaneously a significantly effective physiological elevation of the plasma colloid osmotic pressure.

The Donnan effect of the plasma proteins causes the osmotic pressure to be about 50 percent greater than that caused by proteins alone. This results from the fact that the protein molecules themselves cannot readily diffuse through the semi-permeable capillary membrane and the electronegative charges on the proteins, which are negative ions, attract positive ions (cations), mostly sodium ions but also include all the other cations in the extracellular fluid, and thus balance those charges. Osmotic pressure is determined by the numbers of particles per unit volume of fluid, not the weight of the particles. Those extra cations increase the number of osmotically active substances wherever the dissolved proteins occur and thus increase the total colloid osmotic pressure. Thus the Donnan equilibrium effect becomes more significant the higher the concentration of proteins, therefore justifying the requisite daily intake of NaCl to provide a racing or near maximally exercising horse about 1500 mEq $Na^+$, and the daily intake of KCl to provide about 6400 mEq of $K^+$ and MgO to provide about 3300 mEq $Mg^{2+}$ and about 4200 mEq urea when this invention is consumed daily at a dosage regimen sufficient to produce maximum therapeutic effect and thus effectively provision for the prevention or elimination of EIPH.

EXAMPLE 5

This example illustrates the effectiveness of the daily oral administration of powdered urea—KCl—MgO formulation to a 9 year old Standardbred gelding, 480 kg body weight, with a long documented history of EIPH occurring during racing. Prior to each race, an intravenous bleeder injection was administered and no evidence of EIPH occurred until what was the animal's last race of the spring race meet. During that last race, an obvious aberration of the animal's usual performance became evident. Between 45 and 60 minutes postrace, an endoscopic examination was performed and a positive diagnosis made of EIPH with the presence of copious amounts of free-flowing blood in the bronchi and trachea. Further verification of the EIPH episode was documented several days later by a tracheobronchial wash which was cytologically examined and the presence observed of a predominance of macrophages which often contain hemosiderin, i.e. said erophages, hemosiderophages, thus confirming with absolute certainty the presence of a previous EIPH episode in this animal which occurred during racing. Subsequently, the animal was removed from the race track and rested for five months. Upon returning to training, in anticipation of racing, the daily feed intake consisted of about 14 pounds (6.4 kg) of alfalfa hay, about 8 pounds (3.6 kg) of whole oats and about 8 pounds (3.6 kg) of commercial mixed grain plus supplemental NaCl and a mineral-vitamin mixture. The powdered preparation of urea—KCl—MgO was added to the daily grain ration at a level of about 2.5 weight percent of urea, about 1.5 weight percent of KCl and about 0.1 weight percent of MgO. At this level of feed intake, the test animal was provided with a total daily intake of about 3,000 mEq of urea and about 6400 mEq $K^+$. NaCl was supplemented to provide the test animal with a total daily intake of about 1550 mEq $Na^+$.

The effective daily dosage administered of this invention was between about 320 mg/kg body weight and about 380 mg/kg body weight for urea, for KCl was between about 185 mg/kg body weight and about 250 mg/kg body weight and for MgO was between about 6 mg/kg body weight and about 7 mg/kg body weight. The dosage regimen employed during this test was sufficient to ensure maximum therapeutic response for the prevention or elimination of EIPH in racing or maximally exercising horses.

To ascertain if any pathophysiological alterations occurred during the test and became apparent in the hemogram and biochemical profile of the test animal, a series of blood samples were collected: (1) post-rest/pre-training (Day 0); (2) mid-training (Day 49); (3) post qualification race (Day 137); (4) training following qualification race (Day 178). The results are listed below.

|  | Blood Sample | | | | |
| --- | --- | --- | --- | --- | --- |
|  | 1<br>Day 0 | 2<br>Day 49 | 3<br>Day 137 | 4<br>Day 178 | Units |
| Hematology and Biochemistry | | | | | |
| White cell count | 9.7 | 8.0 | 7.8 | 7.6 | th/mm$^3$ |
| Red cell count | 8.0 | 6.9 | 7.3 | 8.3 | mil/mm$^3$ |
| Hemoglobin | 14.2 | 11.9 | 13.2 | 13.7 | g/dl |
| Hematocrit | 37.6 | 32.7 | 35.2 | 37.6 | % |
| Platelet count | 200 | 170 | 190 | 190 | th/mm$^3$ |
| Glucose | 94 | 114 H | 85 | 84 | mg/dl |
| Blood urea nitrogen | 28 H* | 27 H | 25 | 24 | mg/dl |
| Creatinine | 1.5 | 1.6 | 1.7 | 1.6 | mg/dl |
| Sodium | 139 | 141 | 140 | 141 | meq/dl |
| Potassium | 3.8 | 3.9 | 3.7 | 3.9 | meq/dl |
| Calcium | 12.4 | 11.7 | 11.2 | 11.8 | mg/dl |
| Phosphorus | 2.8 L | 3.9 | 3.1 | 3.2 | mg/dl |
| Total protein | 7.0 | 6.6 | 7.5 | 7.5 | g/dl |
| Albumin | 3.3 | 3.2 | 3.3 | 3.5 | g/dl |
| Globulin | 3.7 | 3.4 | 4.2 H | 4.0 H | g/dl |
| Bilirubin total | 1.2 | 1.5 | 3.0 | 2.7 | mg/dl |
| Albumin/Globulin ratio | 0.9 | 0.9 | 0.8 | 0.9 | |
| Calculated osmolality | 281 | 285 | 281 | 282 | |
| Chloride | 101 | 105 | 102 | 103 | meq/l |
| Carbon dioxide | 28 | 25 | 26 | 26 | meq/l |
| Anion gap | 10 | 11 | 12 | 12 | |
| Cholesterol | 88 | 85 | 89 | 90 | mg/dl |

-continued

| | Blood Sample | | | | |
|---|---|---|---|---|---|
| | 1<br>Day 0 | 2<br>Day 49 | 3<br>Day 137 | 4<br>Day 178 | Units |
| Protein Electrophoresis | | | | | |
| Albumin | 3.00 | 2.80 | 3.50 | 3.50 | g/dl |
| Alpha-1 Globulin | 0.03 L | 0.20 H | 0.10 H | 0.10 H | g/dl |
| Alpha-2 Globulin | 0.80 | 0.20 L | 0.50 | 0.40 | g/dl |
| Beta-1 Globulin | 0.60 | 0.60 | 0.70 | 0.60 | g/dl |
| Beta-2 Globulin | 0.50 | 0.70 | 0.60 | 0.50 | g/dl |
| Gamma Globulin | 2.10 H | 2.50 H | 2.10 H | 2.30 H | g/dl |

*L - Lower than normal value
H - Higher than normal value

On Day 0, the hemogram and biochemistry values obtained were essentially normal for a rested horse entering race training. The exception to the essentially normal profile was the markedly elevated globulin portion of the total protein. Plasma protein electrophoresis revealed, surprisingly, even after five months of pasture rest, that the alpha-1 globulin fraction was of a lower than normal value which was comparable to the value found in some horses at the finish of a multi-race meet. Even more surprising was the obvious grossly above normal elevation of the gamma globulin fraction of the plama protein with a complete absence of any abnormal clinical or physical signs. Upon reviewing these electrophoretic results, the clinical pathological diagnosis of this data was polyclonal gammopathy.

Midway through the race training period (Day 49), the hematological and biochemical values were determined from the second blood sample. The values obtained were slightly lower than found in the first blood sample (Day 0) but were essentially normal except for the still large above normal elevation of the globulin portion of the plasma protein. Electrophoretic fractionation of the plasma protein of this blood sample revealed an elevated and a diminished concentration of the alpha-1 and alpha-2 globulin fractions, respectively. This phenomena has previously been observed to occur when this invention was consumed daily at a level sufficient to produce maximum therapeutic response for the prevention or elimination of EIPH in racing or maximally exercising horses. The gamma globulin fraction of the plasma protein was still grossly elevated, and thus the clinicopathological diagnosis was made again of polyclonal gammopathy.

Two days after an attempted qualifying race, when an unacceptable time of 2:13 for the mile was attained, a third blood sample (Day 137) was collected for hematological and biochemistry analysis. Again, with the exception of the globulin fraction of the plasma protein, the hemogram and remaining biochemical values were within normal limits. Electrophoretic analysis revealed the usual increase in albumin concentration which occurs after the initiation of competitive racing. The alpha-1 globulin fraction, although decreased in concentration from sample two (Day 49), was still elevated above normal level, but the concentration recorded was comparable to that occurring in the long-term daily feeding of a racing test animal. The alpha-2 globulin level, previously a lower than normal value, had now increased to a concentration within the normal range. The gamma globulin fraction was still elevated prominently to a higher than normal value, thus eliciting the continual clinicopathological diagnosis of polyclonal gammopathy.

The fourth blood sample (Day 178) was collected 41 days after the unsuccessful qualifying race and after much more endurance training and eight race-works. With the exception of the increased globulin concentration of the plasma protein, the remainder of the hemogram and biochemical values in this blood sample were within the normal range. Plasma protein electrophoresis revealed, as previously recorded in sample 3 (Day 137), an increased alpha-1 globulin, a normal concentration of alpha-2, beta-1 and beta-2 globulin fractions resulting in the repetitive clinicopathological diagnosis of polyclonal gammopathy.

At no time during the entire 187 day test period did the test animal show any hesitation or refusal to consume this invention when it was admixed into the daily grain ration. Nor was there ever any clinical indication evident of gastrointestinal upset or symptoms of physical discomfort or colic that could be attributed to the daily consumption of this invention.

About 45 minutes after completion of the unsuccessful qualifying race, which the test animal completed with a speed of about 726 meters per minute, an endoscopic examination of the lungs was performed by the official racetrack veterinarian to determine if the presence of EIPH was the primary factor influencing the slow racing time attained. The numerical classification of the performed endoscopic examination was Grade 0—no blood present. The test animal avidly consumed water when it was offered after completion of the qualifying race. As this example particularly illustrates, especially with the absence of endoscopic documentation of the most common presenting signs of EIPH, it is manifestly logical to conclude that other abnormal physiological factors are primarily responsible for causally influencing the resulting slow race time performed by the test animal.

Following the unsuccessful qualifying race, in which the test animal failed to reach a minimum speed of 754 meters per minute, the said animal was further endurance trained and race-worked eight times in the following 41 days. A racework consists of a warm-up mile at a speed of about 644 meters per minute, followed by a 30 minute rest and then an all-outspeed mile. In all eight of the all-out-speed miles, the minimum qualifying speed for racing of about 754 meters per minute was not reached, the speed produced ranged between about 695 meters per minute and about 721 meters per minute. However, at no time during or following these eight all-outspeed miles did the test animal show any characteristic symptoms of EIPH, ie. swallowing, coughing or dyspnea, and it always readily consumed water when offered after these raceworks.

From these results, it specifically appears and is logical to conclude that the daily oral administration of this invention at the aforementioned dosage regimen to a 9 year old Standardbred gelding, having a long documented history of EIPH occurring while racing and a currently ongoing clinical pathological diagnosis of polyclonal gammopathy, produces the anticipated maximum therapeutic response which is to effectively prevent or eliminate EIPH in racing or maximally exercising horses.

EXAMPLE 6

Racing or maximally exercising horses generally consume a total daily feed ration comprised of about 12 to 14 percent crude protein which is acknowledged as being an adequate and acceptable level of protein intake. Even with this level of protein in the ration the globulin fraction of the plasma proteins is surely and irrevocably reduced with continuous racing of the said animals during the course of a long multi-race meet.

A surprising discovery is that the levels of both the albumin and globulin fractions of the plasma protein are substantially increased when this invention is administered daily to racing horses at a dosage regimen sufficient to produce maximum therapeutic response for the prevention or elimination of EIPH. The quantity of feed nitrogen utilization and retention is significantly enhanced by intestinal microflora utilizing the NPN, ie. urea, present in this invention.

The albumin and globulin fractions of plasma protein were determined through the laboratory technique of protein electrophoresis and the results listed below for each blood sample collected. Single blood samples were obtained from a 4 year old Standardbred and an 8 year old Thoroughbred following completion of their respective six-months long race meets and consuming the usual type of diet fed to racing horses. For comparison, a series of blood samples were procured from a 3 year old Standardbred at various times during an ongoing multi-race meet while consuming this invention supplemented into the usual type of ration fed to a racing horse: (1) post-training and pre-racing (Day 0); (2) early racing (Day 30); (3) mid-racing (Day 72); and, (4) late mid-racing (Day 107).

the lymphoid tissue and other cells of the reticuloendothelial system. The principal function of albumin is to provide colloid osmotic pressure which prevents plasma loss from capillaries. The globulins also perform a number of enzymatic functions in the plasma but principally they are responsible for the natural and acquired immunity against invading organisms.

Regardless of the diet available, the albumin content of plasma protein is firstly and sizeably increased when a horse begins continuous racing. Unless excess amino acids become available from the diet, the globulin fraction of plasma protein, with the exception of the immunogenic gamma globulin fraction, found in racing horses is substantially reduced with continuous racing.

Even though the colloid osmotic pressure of the plasma is a weak osmotic force, it plays an exceedingly important role in the maintenance of normal blood and interstitial fluid volumes. Since 1 gram of albumin contains twice as many molecules as 1 gram of globulin, each gram of albumin exerts twice as much osmotic pressure as each gram of globulin. Since there is almost 50 percent more albumin than globulin, about 60 percent of the total osmotic pressure of the plasma in racing horses results from the albumin fraction and about 40 percent from the globulins. Capillary hemodynamics in non-racing horses are mainly influenced by albumin. However, a further discovery is that in racing horses the globulins, and primarily the alpha-1 globulin fraction, substantially effect the total colloid osmotic pressure of the plasma. The alpha-1 globulin level is increased between about 3 to about 10 times more in continuously racing horses consuming this invention daily than the level found in continuously racing horses not consuming this invention.

With the daily intake of this invention administered at maximum therapeutic dosage to prevent or eliminate EIPH the globulin fraction of the plasma proteins becomes substantially increased in racing horses. The concentration of the alpha-1 globulin fraction especially becomes increased many times more than the other

| Protein Electrophoresis | Standardbred Post-race Meet | Thoroughbred Post race Meet | Standardbred-Racing | | | | Units |
| --- | --- | --- | --- | --- | --- | --- | --- |
| | | | Pre-Race Day 0 | Early Race Day 30 | Mid-race Day 72 | Late Mid-Race Day 107 | |
| Albumin | 3.70 | 3.60 | 3.30 | 3.60 | 3.40 | 3.80 | g/dl |
| Alpha-1 Globulin | 0.03 L* | 0.10 H | 0.10 H | 0.30 H | 0.20 H | 0.10 H | g/dl |
| Alpha-2 Globulin | 0.50 | 0.40 | 0.40 | 0.10 L | 0.10 L | 0.40 | g/dl |
| Beta-1 Globulin | 0.30 L | 0.30 L | 0.50 | 0.40 | 0.40 | 0.60 | g/dl |
| Beta-2 Globulin | 0.50 | 0.30 | 0.30 | 0.50 | 0.60 | 0.30 | g/dl |
| Gamma Globulin | 1.20 | 1.10 | 1.40 | 1.20 | 1.20 | 1.20 | g/dl |

*L - Lower than normal value
H - Higher than normal value

The rate of synthesis of plasma protein by the liver depends on the concentration of amino acid in the blood. Consequently, the concentration of proteins becomes reduced whenever an appropriate supply of amino acid is not available. Conversely, when excess proteins are available in the plasma but insufficient proteins are available in the cells, the plasma proteins are used to form tissue cells. Undoubtedly, this is the sequence that is occurring when the plasma protein level is measured in horses that are continuously raced and consume a normal performance-type feed ration. Essentially, all the albumin of the plasma proteins, as well as 60 to 80 percent of the globulins, are formed in the liver. The remainder of the globulins, mainly the gamma globulins which constitute the antibodies, are formed in globulin fractions. The colloid osmotic pressure exerted by alpha-1 globulin at every plasma protein concentration is more than twice that produced by the same plasma protein concentration of albumin, thus positively influencing the non-appearance of EIPH and the markedly improved performance of racing or maximally exercising horses supplemented daily with this invention.

EXAMPLE 7

This example illustrates the preparation and utilization of specialized forms of this invention that can be alternately and adjunctly used for the prevention or elimination of EIPH in racing or maximally exercising horses. The test was conducted to demonstrate that various physical forms of this invention produce identical observable physiological effects, ie. increased water intake and increased urine excretion, as observed in the safest and most practical methods of administration, namely, as dry formulations or aqueous solutions added to the daily feed ration and voluntarily consumed by the horse.

Hard capsules were prepared from the following formulation:
225 g of urea
160 g of potassium chloride The above ingredients were thoroughly mixed with each other and the mixture was filled into gelatin capsules. Each capsule contained about 28.6 g of the composition and thus about 16.6 g of urea, about 11.8 g of KCl and about 800 mEq $Mg^{2+}$. The capsules were administered on a daily basis to horses.

Tablets were prepared from the following formulation:
225 g of urea
160 g of potassium chloride
5 g of magnesium stearate The active ingredients were thoroughly mixed with magnesium stearate and compressed into tablets, each weighing about 100 g and containing about 58 g of urea and about 41 g of KCl. The tablets were considered suitable for administration to horses.

Compositions defined above are readily absorbed into the bloodstream after reaching the stomach and intestine when given orally. The objects provide an alternate or adjunct method of prophylactic or curative treatment of EIPH in racing or maximally exercising horses.

A series of tests were performed on each of two horses, one a 4 year old Thoroughbred gelding, 431 kg body weight, the other a 4 year old Standardbred gelding, 428 kg body weight, using the above formulations and documenting the resulting observable physiological effects. Each test period duration was seven days with a recovery period of the same length of time.

During the two tests, the Thoroughbred animal received an effective daily dosage of urea of between about 475 mg/kg body weight to about 535 mg/kg body weight and between about 225 mg/kg body weight and about 380 mg/kg body weight of KCl, while the Standardbred was given about 485 mg/kg body weight and about 540 mg/kg body weight of urea and between about 230 mg/kg body weight and about 385 mg/kg body weight of KCl. Each test animal received supplemental NaCl to provide a total daily intake of about 1400 mEq $Na^+$. The total daily feed intake along with the administration of the specialized forms of this invention provided each test animal with a daily intake of about 3800 mEq of urea and about 6300 mEq of $K^+$. The animal's daily feed provided a total daily intake of about 900 mEq of $Mg^{2+}$.

In both test animals, during these tests, noticeable physiological effects, ie. increased water intake and increased urine excretion, occurred when the tablets and hard capsules were given orally. By the second day after the start of oral administration of these formulations, the physiological effects became noticeably elevated and remained at that level until the third day after completion of the tests, at which time, both water intake and urine excretion decreased to pre-test levels.

The two test horses did not react adversely to the oral administration of the specialized forms of this invention.

No evidence of colic or gastrointestinal upset occurred in these horses during these tests.

It is evident from this example that regardless of the physical form of this invention, the occurrence of noticeable physiological effects, after oral administration, were identical whether the horse was racing, maximally exercising or in a maintenance condition. It thus follows that the etiopathogenesis of EIPH in racing or maximally exercising horses could also be prophylactically or curatively treated by oral administration of specialized forms of this invention.

While I have described and given examples of preferred embodiments of my invention, it will be apparent to those skilled in the art that changes and modifications may be made without departing from my invention in its broader aspects. I therefore intend the appended claims to cover all such changes and modifications as fall within the true spirit and scope of my invention.

I claim:

1. A method for treating or preventing exercise-induced pulmonary hemorrhage in an equine specimen comprising the steps of:
   providing an equine specimen which has experienced exercise-induced pulmonary hemorrhage or is prone to the development of exercise-induced pulmonary hemorrhage; and
   administering a therapeutic agent to the equine specimen, the therapeutic agent comprising a first chemical additive selected from the group consisting of urea and pharmaceutically acceptable salts thereof, and a second chemical additive comprising an alkaline potassium salt selected from the group consisting of potassium chloride, potassium citrate, potassium phosphate, potassium nitrate, potassium sulfate, potassium acetate, potassium silicate and potassium gluconate.

2. A method according to claim 1 wherein the first chemical additive is in the free base form.

3. A method according to claim 1 wherein the alkaline potassium salt is potassium chloride.

4. A method according to claim 1 wherein the therapeutic agent comprises about 1 to about 65 percent by weight first chemical additive, and about 0.05 to about 50 percent by weight alkaline potassium salt.

5. A method according to claim 1 wherein the alkaline potassium salt is present in the therapeutic agent in an amount ranging from about 0.05 to about 45 percent by weight.

6. A method according to claim 1 wherein the alkaline potassium salt is present in the therapeutic agent in an amount ranging from about 0.05 to about 35 percent by weight.

7. A method according to claim 4 wherein the alkaline potassium salt is present in the therapeutic agent in an amount ranging from about 0.25 to about 0.8 parts by weight per 1 part by weight of the first chemical additive.

8. A method according to claim 4 wherein the alkaline potassium salt is present in the therapeutic agent in an amount equal to about 0.6 parts by weight per 1 part by weight of the first chemical additive.

9. A method according to claim 1 wherein the therapeutic agent is incorporated into a feed or liquid composition and is fed to the equine specimen on a daily basis.

10. A method according to claim 1 wherein the therapeutic agent is included in the daily diet of the equine specimen in an amount between about 100 to about 1250 mg/kg body weight of the equine specimen.

11. A method for treating or preventing exercise-induced pulmonary hemorrhage in an equine specimen comprising the steps of:
providing an equine specimen which has experienced exercise-induced pulmonary hemorrhage or is prone to the development of exercise-induced pulmonary hemorrhage; and
administering a therapeutic agent to the equine specimen, the therapeutic agent comprising a firs chemical additive selected from the group consisting of urea and pharmaceutically acceptable salts thereof, a second chemical additive comprising an alkaline potassium salt selected from the group consisting of potassium chloride, potassium citrate, potassium phosphate, potassium nitrate, potassium sulfate, potassium acetate, potassium silicate and potassium gluconate, and a third chemical additive comprising a magnesium oxide, magnesium hydroxide, magnesium phosphate, magnesium sulfate, magnesium acetate, magnesium chloride, magnesium adipate, magnesium acetate, magnesium gluconate, and magnesium carbonate.

12. A method according to claim 11 wherein the therapeutic agent comprises about 1 to about 65 percent by weight first chemical additive, and about 0.05 to about 50 percent by weight alkaline potassium salt.

13. A method according to claim 12 wherein the therapeutic agent comprises about 0.25 to about 25 percent by weight magnesium salt.

14. A method according to claim 11 wherein the magnesium salt is magnesium oxide.

15. A method according to claim 11 wherein the magnesium salt is present in the therapeutic agent in an amount ranging from about 1 to about 25 percent by weight.

16. A method according to claim 11 wherein the magnesium salt is present in the therapeutic agent in an amount ranging from about 1 to about 15 percent by weight.

17. A method according to claim 11 wherein the magnesium salt is present in the therapeutic agent in an amount ranging from about 1 to about 10 percent by weight.

18. A method according to claim 13 wherein the magnesium salt is present in the therapeutic agent in an amount ranging from about 0.05 to about 0.25 parts by weight per 1 part by weight of the first chemical additive.

19. A method according to claim 11 wherein the alkaline potassium salt is present in the therapeutic agent in an amount ranging from about 0.05 to about 45 percent by weight.

20. A method according to claim 11 wherein the alkaline potassium salt is present in the therapeutic agent in an amount ranging from about 0.05 to about 35 percent by weight.

21. A method according to claim 11 or 13 wherein the therapeutic agent is incorporated into a feed or liquid composition and is fed to the equine specimen on a daily basis.

22. A method according to claim 11 or 13 wherein the therapeutic agent is included in the daily diet of the equine specimen in an amount between about 100 to about 1250 mg/kg body weight of the equine specimen.

* * * * *